United States Patent [19]

Kolditz

[11] Patent Number: 5,442,284

[45] Date of Patent: Aug. 15, 1995

[54] PROCESS FOR INSPECTING SPACERS OF HEAT EXCHANGER TUBES IN A HEAT EXCHANGER

[75] Inventor: Joachim Kolditz, Talheim, Germany

[73] Assignee: Gemeinschaftskernkraftwerk Neckar GmbH, Neckarwestheim, Germany

[21] Appl. No.: 56,433

[22] PCT Filed: Jun. 30, 1993

[86] PCT No.: PCT/EP92/01997

§ 371 Date: Jun. 30, 1993

§ 102(e) Date: Jun. 30, 1993

[87] PCT Pub. No.: WO93/05391

PCT Pub. Date: Mar. 18, 1993

[30] Foreign Application Priority Data

Sep. 2, 1991 [DE] Germany .............. 41 29 153.0

[51] Int. Cl.$^6$ .............. G01N 27/90; G01B 5/20; G01B 7/26; G21C 17/00

[52] U.S. Cl. .............. 324/220; 33/302; 33/544.1; 376/249

[58] Field of Search .............. 324/219–221, 324/207.18, 225, 238; 33/302, 501.9, 542–544; 73/623, 151, 152; 376/245, 249, 258

[56] References Cited

U.S. PATENT DOCUMENTS

| | | | |
|---|---|---|---|
| 3,302,105 | 1/1967 | Libby et al. | |
| 3,694,740 | 9/1972 | Bergstrand | 324/227 |
| 4,182,985 | 1/1980 | DeWolfe et al. | 324/220 |
| 4,194,149 | 3/1980 | Holt et al. | 324/220 |
| 4,235,020 | 11/1980 | Davis et al. | 324/220 X |
| 4,341,113 | 7/1982 | Gutzwiller, Jr. | 324/220 X |
| 4,625,165 | 11/1986 | Rothstein | 324/220 |
| 4,687,992 | 8/1987 | Bernus et al. | 324/220 |
| 4,814,702 | 3/1989 | Driggers et al. | 324/220 X |
| 4,851,773 | 7/1989 | Rothstein | 324/220 X |
| 4,876,506 | 10/1989 | Brown et al. | 324/220 |
| 5,237,270 | 8/1993 | Ceceo et al. | 324/220 |

FOREIGN PATENT DOCUMENTS

| | | |
|---|---|---|
| 0156020 | 12/1984 | European Pat. Off. |
| 0224230 | 11/1986 | European Pat. Off. |
| 0259669 | 8/1987 | European Pat. Off. |
| 3447781 | 12/1984 | Germany |
| 2010492 | 10/1978 | United Kingdom |

*Primary Examiner*—Sandra L. O'Shea
*Assistant Examiner*—Jay M. Patidar
*Attorney, Agent, or Firm*—Robert W. Becker & Associates

[57] ABSTRACT

In a method of inspecting heat exchanger tubes of a heat exchanger in which the heat exchanger tubes are fixed in position by spacers and serve to transfer heat from a first medium to a second medium that is fluid-tightly separated from the first medium, a measuring probe is introduced into an heat exchanger tube to be inspected. A wall section of the heat exchanger tube is subjected to an electromagnetic alternating field generated by the measuring probe resulting in local eddy currents within the subjected wall section. An eddy current sensor that is rotatable in the circumferential direction of the heat exchanger tube is guided in the longitudinal direction of the subjected wall section of the heat exchanger tube. A voltage signal induced by the eddy currents within the wall section is picked up with the eddy current sensor. The voltage signal varies locally as a function of the condition of the material of the wall section, the thickness of the wall section, and the presence of a spacer. The voltage signals induced by a spacer is saved and evaluated by comparison with a reference signal.

4 Claims, No Drawings

PROCESS FOR INSPECTING SPACERS OF HEAT EXCHANGER TUBES IN A HEAT EXCHANGER

BACKGROUND OF THE INVENTION

The invention relates to a method for inspecting heat exchanger tubes of a heat exchanger according to the preamble of claim 1.

Especially of a steam generator within a primary circuit of a power plant, with which heat exchanger a heat transfer from a first medium to a second medium that is gas- and liquid-tightly separated from the first medium is performed, with the tubes fixed in their position by spacers, wherein a measuring probe is inserted into the tube to be inspected, with which probe the tube section to be inspected is subjected to an electromagnetic alternating field of a predetermined frequency, and wherein the local eddy currents generated within the tube section induce a voltage signal within an eddy current sensor that is slidable in the longitudinal direction of the tube and rotatable in the circumferential direction of the tube, the voltage signal varying locally according to the condition of the material and the thickness of the wall section. A nuclear power plant has approximately 3,000 to 6,000 heat exchanger tubes which are fixed in their position over their length with five to ten spacers. The spacers have predetermined fixed distances and support one tube over a portion of its circumference. When the spacers are loosened or displaced during operation, the heat exchanger tubes can be induced to perform undesirable vibrations which result in a premature material fatigue, respectively, in a wall thickness reduction of the tube. The vibrations can be so strong that the heat exchanger tubes mechanically impact one another possibly causing a leak. However, especially in the case of nuclear power plants it is a primary requirement that the radioactively loaded primary circuit is gas- and liquid-tightly separated from the secondary circuit. Accordingly, such a heat exchanger is subjected regularly to repeated inspections. Each individual heat exchanger tube is inspected with an eddycurrent measuring probe which is inserted into the tube to be inspected. An electromagnetic alternating field of a predeterminable frequency generates within the tube wall local eddy currents which induce voltage signals in a sensor that is entrained with the probe. By rotating the sensor in the circumferential direction of the tube and by guiding it along the longitudinal direction of the heat exchanger tube, each location of the tube wall is inspected with the eddy current sensor. For a uniform wall thickness and homogenous material the eddy current sensor emits a uniform, approximately constant signal. However, wall thickness reductions, material fractures etc. lead to changed sensor exit signals and can thus be recognized and locally fixed. Changes of the sensor exit signal caused by other effects, as, for example, the spacers, are suppressed in the known method because they prevent an evaluation of the condition of the wall. Since the position of the spacers in the longitudinal direction as well as within the circumferential direction of the tube is known, the suppression of such a disturbing signal is easily accomplished.

It is however disadvantageous that with the known method only damage that has already occurred due to a loose or wrongly positioned spacer can be detected. It is furthermore possible that initially only one spacer along one of the heat exchanger tubes is loose and that the resulting vibrations of the tube do not lead immediately to any significant changes of the wall thickness, respectively, of the condition of the tube material. This critical location within the heat exchanger thus cannot be detected with the known method. When in addition another spacer neighboring the first loose spacer comes loose, a relatively long section of the heat exchanger tube is insufficiently supported and thus prone to considerable vibrations, which within a short period of time, can result in a fracture and thus in a radioactive contamination of the secondary circuit. In practice, such a case has occurred in a nuclear power plant in Japan.

It is therefore an object of the present invention to provide a method for inspecting heat exchanger tubes of a heat exchanger with which the fixation and the spacial position of each individual spacer can be detected.

SUMMARY OF THE INVENTION

The method of inspecting heat exchanger tubes of a heat exchanger, the heat exchanger tubes fixed in position by spacers and serving to transfer heat from a first medium to a second medium, the second medium being fluid-tightly separated from the first medium, according to the present invention is primarily characterized by the following steps:
  introducing a measuring probe into an heat exchanger tube to be inspected;
  subjecting a wall section of the heat exchanger tube to an electromagnetic alternating field Generated by the measuring probe resulting in local eddy currents within the subjected wall section;
  guiding an eddy current sensor, rotatable in the circumferential direction of the heat exchanger tube, in the longitudinal direction of the subjected wall section of the heat exchanger tube;
  picking up a voltage signal induced by the eddy currents within the wall section with the eddy current sensor, the voltage signal varying locally as a function of a condition of the material of the wall section, a thickness of the wall section, and the presence of a spacer;
  saving voltage signals induced by a spacer of the wall section; and
  evaluating the saved voltage signals by comparison with a reference signal.

Preferably, the method further comprises the step of employing the amplitude of the saved voltage signals for the evaluating step. Alternatively, the shape of the saved voltage signals can be used for the evaluating step.

Advantageously, the reference signal is generated as an arithmetic mean of the sum of the initial voltage signals of the heat exchanger and all induced voltage signals are compared with the arithmetic mean and recorded according to a Gaussian curve.

Expediently, the method further comprises the step of performing the evaluation with a computer.

DESCRIPTION OF THE PREFERRED EMBODIMENTS

The voltage signal of the sensor which results from local sensing of the wall and is changed by a spacer is saved, and all signals induced by the spacers of the heat exchanger are evaluated by comparison to a reference signal. The method is based on the finding that a spacer fixedly connected to the heat exchanger tube results in an initial sensor signal provides a reference signal and that the eddy currents that are induced are disturbed when the spacer changes its position or is spaced with play to the tube wall, thus resulting in a different voltage signal.

Experiments have shown that the voltage signal induced within the eddy current sensor within the area of the spacer is changed with respect to its shape and amplitude as a function of the spacial position of the spacer as well as of an optional gap between the spacer and the tube.

When upon comparison significant deviations of the reference signal result it is known that with greatest probability an irregularly positioned spacer is present. Since the spacer signals are saved consecutively, the defective spacer can be identified as the $n^{TH}$ spacer on the $i^{TH}$ heat exchanger tube.

For a heat exchanger with approximately 5,000 heat exchanger tubes and five to ten spacers for each tube approximately 25,000 to 50,000 spacer signals must be evaluated. Advantageously it is suggested to generate a reference signal as the arithmetic mean of the saved initial voltage signals of a heat exchanger and to compare all induced voltage signals with this reference signal. As a function of this comparison the individual induced voltage signals are recorded as a Gaussian curve as a function of their standard deviation. By predetermining a limit for the standard deviation it is then possible to recognize voltage signals which have a significant deviation and surpass the predetermined limit, thereby indicating a high probability of a wrongly positioned spacer.

Since for such an inspection of a heat exchanger a great amount of data must be processed, the evaluation of the saved voltage signals is preferably performed by a computer.

With the inventive method incorrectly positioned spacers can be detected in time and countermeasures can be taken before secondary damage at the heat exchanger tubes can be detected. The gas- and liquid-tight separation of primary circuit and secondary circuit, especially for steam generators within a nuclear power plant, can therefore be ensured with great reliability.

The present invention is, of course, in no way restricted to the specific disclosure of the specification and drawings, but also encompasses any modifications within the scope of the appended claims.

What I claim is:

1. A method of inspecting spacers of heat exchanger tubes of a heat exchanger, the heat exchanger tubes fixed in position by spacers and serving to transfer heat from a first medium to a second medium, the second medium being fluid-tightly separated from the first medium, said method comprising the steps of:
   introducing a measuring probe into an heat exchanger tube to be inspected;
   subjecting a wall section of the heat exchanger tube and the spacer located outside the heat exchanger tube to an electromagnetic alternating field generated by the measuring probe resulting in local eddy currents within the subjected wall section and the spacer;
   guiding an eddy current sensor, rotatable in the circumferential direction of the heat exchanger tube, in the longitudinal direction of the subjected wall section of the heat exchanger tube;
   picking up a voltage signal, induced by the eddy currents within the wall section and the spacer, with the eddy current sensor, the voltage signal varying locally as a function of the eddy currents that are affected by a condition of the material of the wall section, a thickness of the wall section, the gap between the spacer and the heat exchanger tube, and the construction of the spacer;
   recording the voltage signals induced by the spacer of the wall section in a computer;
   generating a reference signal as an arithmetic mean of the sum of the voltage signals of the heat exchanger generated after manufacturing the heat exchanger; and
   comparing all recorded voltage signals with the arithmetic mean and detecting those ones of the recorded voltage signals which surpass a preset limit for the standard deviation of a Gaussian curve of the recorded voltage signals and indicate wrongly positioned spacers.

2. A method according to claim 1, further comprising the step of:
   employing an amplitude of the recorded voltage signals for the comparing step.

3. A method according to claim 1, further comprising the step of:
   employing a shape of the recorded voltage signals for the comparing step.

4. A method according to claim 1, further comprising the step of:
   performing the comparing step with a computer.

* * * * *

UNITED STATES PATENT AND TRADEMARK OFFICE
CERTIFICATE OF CORRECTION

PATENT NO. : 5,442,284
DATED : 15 August 1995
INVENTOR(S) : Kolditz

It is certified that error appears in the above-identified patent and that said Letters Patent is hereby corrected as shown below:

On the title page:

[22] PCT Filed: Aug. 29, 1992

Signed and Sealed this

Twelfth Day of December, 1995

Attest:

BRUCE LEHMAN

Attesting Officer

Commissioner of Patents and Trademarks